United States Patent
Gorges et al.

(10) Patent No.: US 9,320,480 B2
(45) Date of Patent: Apr. 26, 2016

(54) IMAGE PROCESSING METHOD AND SYSTEM FOR 3D DISPLAY OF A PATIENT'S ORGAN

(71) Applicant: General Electric Company, Schenectady, NY (US)

(72) Inventors: Sebastien Gorges, Versailles (FR); Luca Bozzelli, Paris (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 191 days.

(21) Appl. No.: 13/943,832

(22) Filed: Jul. 17, 2013

(65) Prior Publication Data

US 2014/0024929 A1 Jan. 23, 2014

(30) Foreign Application Priority Data

Jul. 17, 2012 (FR) ..................... 12 56908

(51) Int. Cl.
| | | |
|---|---|---|
| *A61B 5/05* | (2006.01) | |
| *A61B 6/12* | (2006.01) | |
| *A61B 6/03* | (2006.01) | |
| *A61B 6/06* | (2006.01) | |
| *A61B 6/00* | (2006.01) | |

(52) U.S. Cl.
CPC ... *A61B 6/12* (2013.01); *A61B 6/03* (2013.01); *A61B 6/06* (2013.01); *A61B 6/4441* (2013.01); *A61B 6/469* (2013.01); *A61B 6/466* (2013.01)

(58) Field of Classification Search
CPC ........ A61B 6/022; A61B 6/0414; A61B 6/06; A61B 6/12; A61B 6/488; A61B 6/502; A61B 6/542; A61B 6/469; G21K 1/04
See application file for complete search history.

(56) References Cited

U.S. PATENT DOCUMENTS

| 8,445,878 B2 * | 5/2013 | Guez .................... 250/505.1 |
|---|---|---|
| 2011/0013742 A1 | 1/2011 | Zaiki et al. |
| 2011/0075799 A1 | 3/2011 | Okada et al. |

FOREIGN PATENT DOCUMENTS

| FR | 2956969 A1 | 9/2011 |
|---|---|---|
| WO | 2005009243 A1 | 2/2005 |

OTHER PUBLICATIONS

Interventional Radiology article, Int J CARS 2010 5, Suppl 1 :S11-S17.

* cited by examiner

*Primary Examiner* — Joel Lamprecht
(74) *Attorney, Agent, or Firm* — GE Global Patent Operation; Marc A. Vivenzio

(57) ABSTRACT

An image processing method for the 3D display of a patient's organ in which a surgical instrument is positioned, using a medical imaging system comprising a rotating C-arm able to be positioned in at least two angular positions, the C-arm comprising a radiation source at one of its ends, a detector at the other of its ends arranged facing the radiation source, and a collimator arranged between the radiation source and the detector and defining an illumination zone, characterized in that the collimator is adjusted according to the angular position of the rotating C-arm to determine the illumination zone so that the radiation only passes through a region surrounding the surgical instrument.

13 Claims, 4 Drawing Sheets

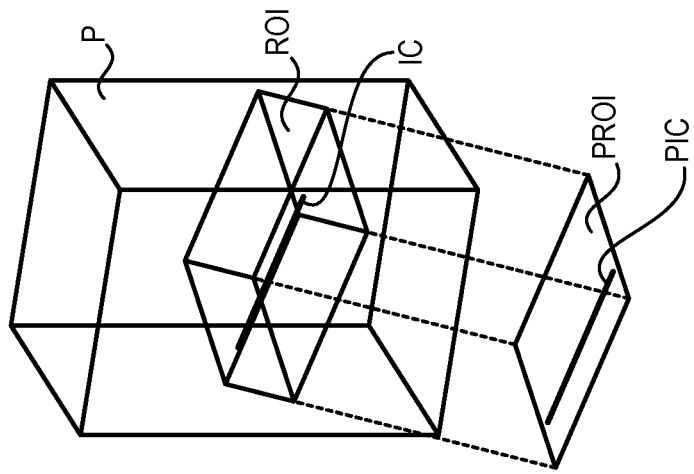
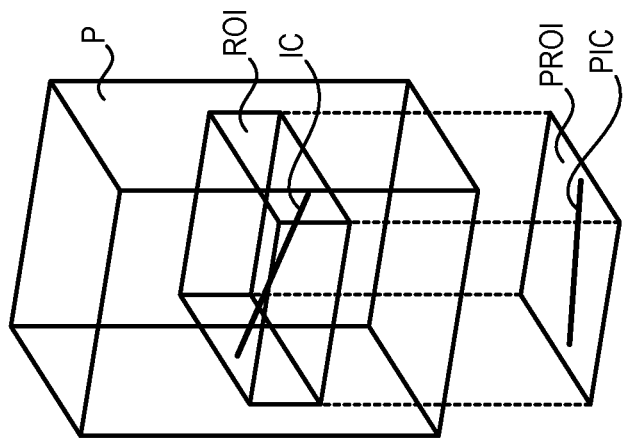
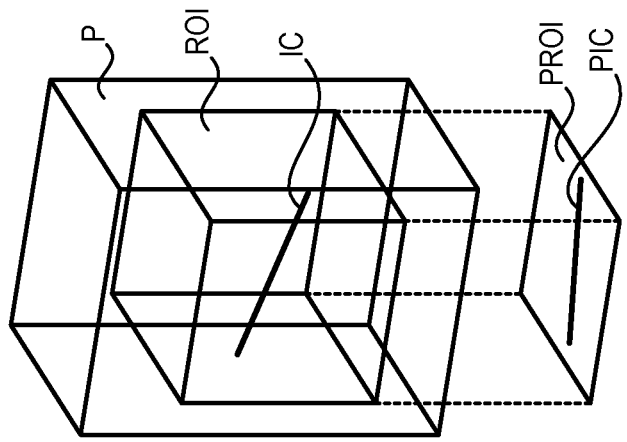

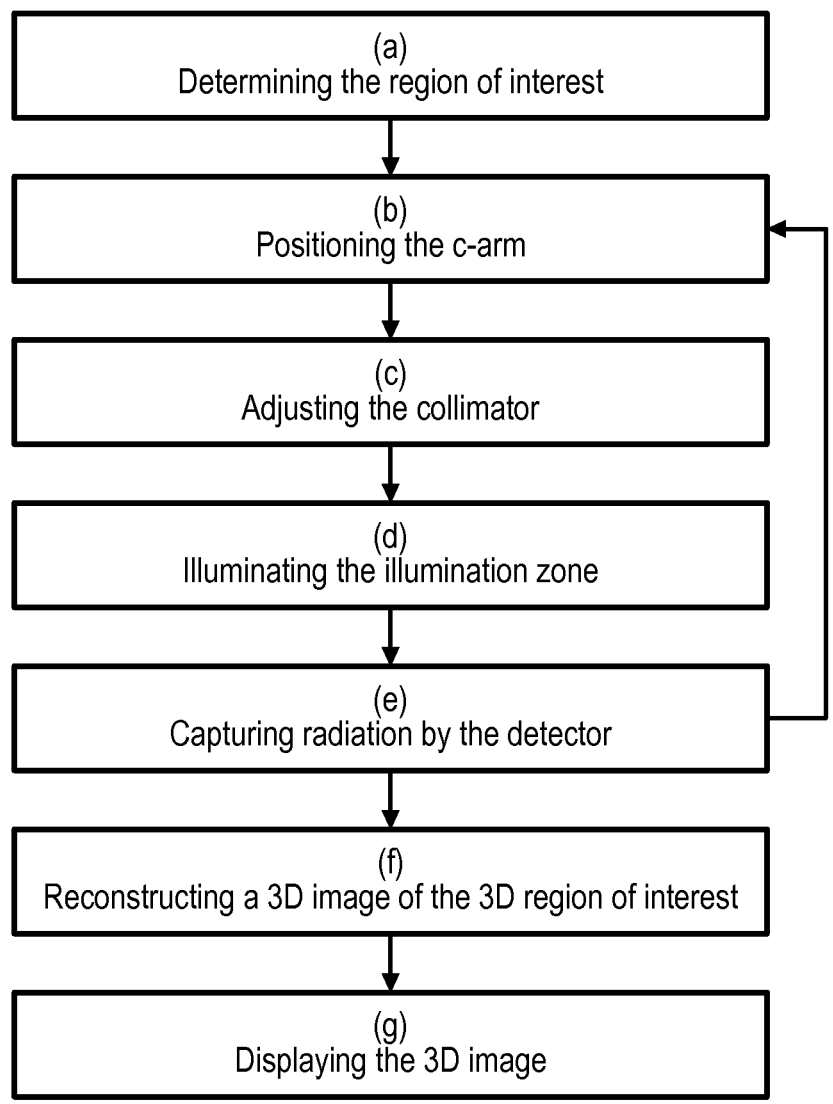

IMAGE PROCESSING METHOD AND SYSTEM FOR 3D DISPLAY OF A PATIENT'S ORGAN

BACKGROUND OF THE INVENTION

Embodiments of the present invention relate to the field of image processing for 3D display of a patient's organ and, more particularly, to the field of image processing for 3D display of a patient's organ in which a surgical instrument is positioned.

Techniques exist which enable real-time visualization of a surgical instrument, in situ, during a surgical procedure, such as a needle, catheter, or straight or spiral wire guide.

Amongst these techniques, fluoroscopy imaging gives real-time knowledge of the position of the surgical instrument. Fluoroscopy imaging enables display of two-dimensional images (2D) of a region of interest in which a surgical instrument has been inserted. Fluoroscopy imaging comprises the use of an X-ray source and a fluorescent monitor between which the patient to be operated on is positioned. The practitioner is then able to track the position of the surgical instrument on the screen and to control the procedure. Modern fluoroscopy imaging, instead of the fluorescent monitor, uses a flat digital sensor and a CCD video camera enabling the recording of 2D images and their display on a screen.

Fluoroscopy imaging only enables the display of 2D images thereby compelling the practitioner to interpret and mentally reconstruct a 3D image in order to determine exactly where the surgical instrument is positioned.

Tomographic imaging enables the construction of images in three dimensions (3D) and provides images corresponding to cross-sectional slices of parts of the patient's body. Thus, the position of the instrument relative to the patient's body can be evaluated.

Although it has numerous advantages, tomographic imaging also has some disadvantages. First, in order to be able to reconstruct a 3D image of the patient' body, several 2D images at different angle positions of a C-arm carrying a radiation source must be acquired. The patient is therefore subjected to radiation doses. In addition, reconstruction of the 3D image is time-consuming. Finally, the display obtained using usual tomographic imaging methods is not optimized. A large volume of the patient's body is reconstructed whereas the practitioner only views those slices which contain the surgical instrument.

SUMMARY OF THE INVENTION

Embodiments of the present invention overcome at least one of the prior art disadvantages presented above.

According to an embodiment of the present invention, there is provided a method for processing images for 3D display of a patient's organ in which a surgical instrument is positioned. The method uses a medical imaging system comprising a rotating C-arm which can be positioned at least at two angular positions, the C-arm comprising a radiation source at one of its ends, a detector at the other of its ends arranged facing the radiation source, and a collimator arranged between the radiation source and the detector and defining an illumination zone, the method comprising (b) positioning the C-arm at an angular position, (c) adjusting the collimator for defining the illumination zone, (d) illuminating the illumination zone by radiation from the radiation source passing through the patient's organ, (e) capturing the radiation which has passed through the organ by the detector to acquire a 2D image, repeating steps (b) to (e) for each angular position of the C-arm, (f) reconstructing a 3D image of the 3D region of interest from the acquired 2D images; and (g) displaying the 3D image, wherein the collimator is adjusted according to the angular position of the C-arm in order to delimit the illumination zone so that the radiation passes only through a zone surrounding the surgical instrument.

According to an embodiment, prior to steps (b) to (e), a region of interest corresponding to the position of the surgical instrument inside the organ can be determined. The collimator also can be adjusted according to the region of interest.

According to an embodiment, the collimator may comprise mobile plates. The position of the mobile plates defines the illumination zone. The region of interest is determined from a first series of full field 2D images of the patent's organ. The first series of full field images are obtained with the C-arm being positioned in a first series of angle positions. In addition, the collimator can be adjusted for another angle position of the C-arm by a theoretical projection of the region of interest onto a full field 2D image corresponding to the other angle position, wherein the position of the mobile plates is calculated from this projection.

In an embodiment, the mobile plates may be mobile in translation along axes orthogonal to their respective face.

In an embodiment, the mobile plates may be mobile in rotation about axes substantially collinear to the main direction of radiation of the source.

In an embodiment, the rotating C-arm may be mobile in rotation about a rotational spin axis corresponding to a head-feet axis of a patient, and about a vertical axis perpendicular to the rotational spin axis and to a craniocaudal axis, wherein the craniocaudal axis passes through the axis of the patient's ears. The angular positions then correspond to positions around the rotational spin axis. Each angular position of the C-arm is adjusted by a rotation about the vertical axis. The C-arm is adjusted to enable the radiation to be substantially perpendicular to a larger surface area of the surgical instrument.

In an embodiment, the 3D region of interest may be a slice parallel to the ground or oblique. Two faces of the 3D region of interest are distant from the surgical instrument by less than 2 cm, in an embodiment less than 1.5 cm, and in an embodiment about 1 cm. In an embodiment, the two faces are the two largest faces of the 3D region of interest.

An embodiment of the present invention is a medical imaging system in the treatment of a patient's organ, in which a surgical instrument is positioned. The medical imaging system comprising a rotating C-arm which can be positioned in at least two angular positions, and a control for positioning the C-arm in an angular position. The C-arm comprising a radiation source at one of its ends capable of emitting radiation to illuminate an illumination zone, a detector at the other of its ends arranged facing the radiation source to capture the radiation, and a collimator arranged between the radiation source and the detector and defining an illumination zone. The collimator is adjustable. Adjustment of the collimator defines the illumination zone. The collimator is adjusted according to the angle position of the C-arm in order to delimit the illumination zone so that the radiation only passes through one region of interest around the surgical instrument.

In an embodiment, the collimator may comprise mobile plates, the position of which defines the illumination zone.

In an embodiment, the mobile plates may be mobile in translation along axes substantially orthogonal to their respective face.

In an embodiment, the mobile plates may be mobile in rotation about axes collinear to the main direction of radiation of the source.

In an embodiment, the rotating C-arm may be mobile in rotation about a rotational spin axis corresponding to the head-feet axis of the patient and about a vertical axis perpendicular to the rotational spin axis and to a craniocaudal axis passing through the axis of the patient's ears.

BRIEF DESCRIPTION OF THE DRAWINGS

Other objectives, characteristics and advantages will become apparent on reading the following description with reference to the drawings given as non-limiting illustrations, among which:

FIG. 2 is a schematic illustration of a 3D-reconstructed image of a region of interest using the tomographic imaging method of the prior art;

FIG. 3 schematically illustrates a 3D-reconstructed image of a region of interest using the image processing method according to an embodiment of the present invention for the 3D display of a patient's organ in which a surgical instrument is positioned, the region of interest being a slice parallel to the ground;

FIG. 4 schematically illustrates the 3D-reconstructed image of the region of interest using the image processing method according to an embodiment of the present invention for the 3D display of a patient's organ in which a surgical instrument is positioned, the region of interest being an oblique slice relative to the ground;

FIG. 7 is a schematic illustration of an example of an image processing method according to an embodiment of the present invention.

DETAILED DESCRIPTION

Figure 1:
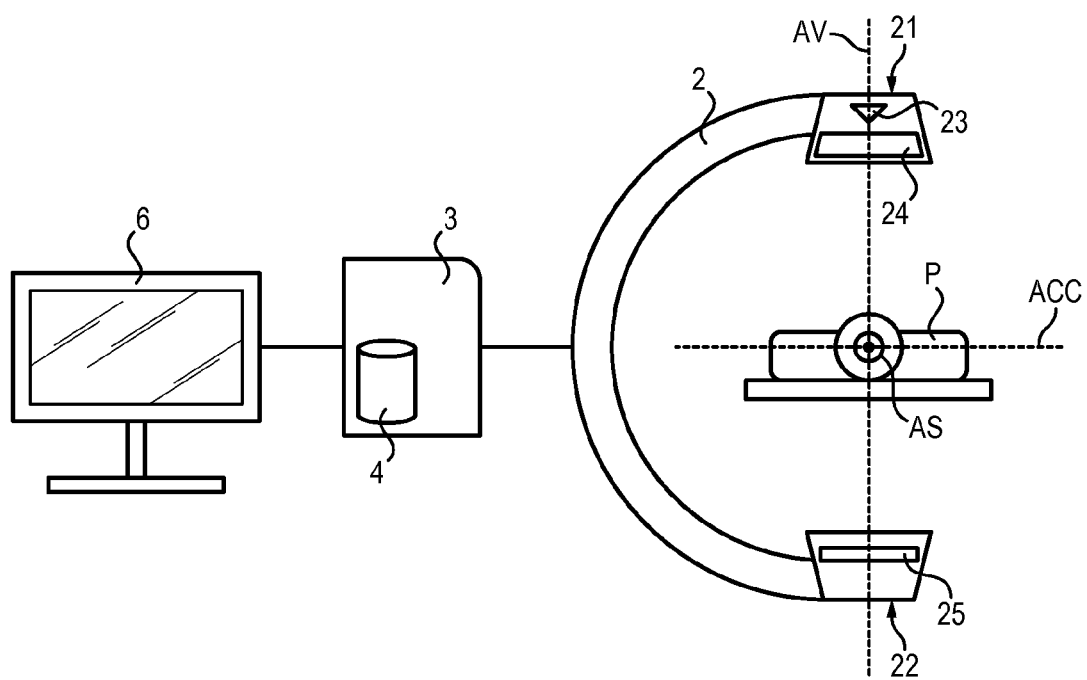
FIG. 1 is a schematic illustration of an example of a medical imaging system according to an embodiment of the present invention.

An embodiment of a medical imaging system is described below with reference to FIG. 1.

The medical imaging system 1 comprises a rotating C-arm 2 which can be positioned in at least two angular positions, and a control 3 for positioning the C-arm 2 in each of the angular positions.

The rotating C-arm 2 is mobile in rotation about a rotation axis AS called a rotational spin axis and which corresponds to a head-feet axis of the patient P. The C-arm 2 may also be mobile in rotation about a vertical axis AV perpendicular to the rotational spin axis AS and to a craniocaudal axis ACC, wherein the craniocaudal axis passes through the ears of a patient P. The latter case enables better positioning of the C-arm 2 in relation to the surgical instrument IC, and, in an embodiment, an elongate surgical instrument having a longitudinal axis AIC, so as to obtain an image of which two opposite edges are substantially parallel to the longitudinal axis AIC.

The C-arm 2, so-called on account of its general C-shape, comprises a radiation source 23 at a first end 21. The radiation source 23 is capable of emitting radiation (e.g. X-rays) to illuminate an illumination zone. The illumination zone is the zone through which the radiation of the radiation source 23 passes.

The C-arm 2 also comprises a detector 25 at a second end 22. The detector 25 is arranged facing the radiation source 23. The detector 25 is capable of capturing the radiation emitted by the radiation source 23 and which has passed through the patient P.

The C-arm 2 also comprises a collimator 24 arranged between the radiation source 23 and the detector 25. The collimator 24 defines the illumination zone. The collimator 24 can be adjusted to optimize the illumination zone, i.e. to achieve minimization of the illumination zone in relation to the medical images it is desired to obtain. The collimator 24 is adjusted according to the angle position of the C-arm 2. It is therefore possible to delimit the illumination zone so that the radiation only passes through a zone surrounding a region of interest ROI comprising the surgical instrument IC.

Figure 5:
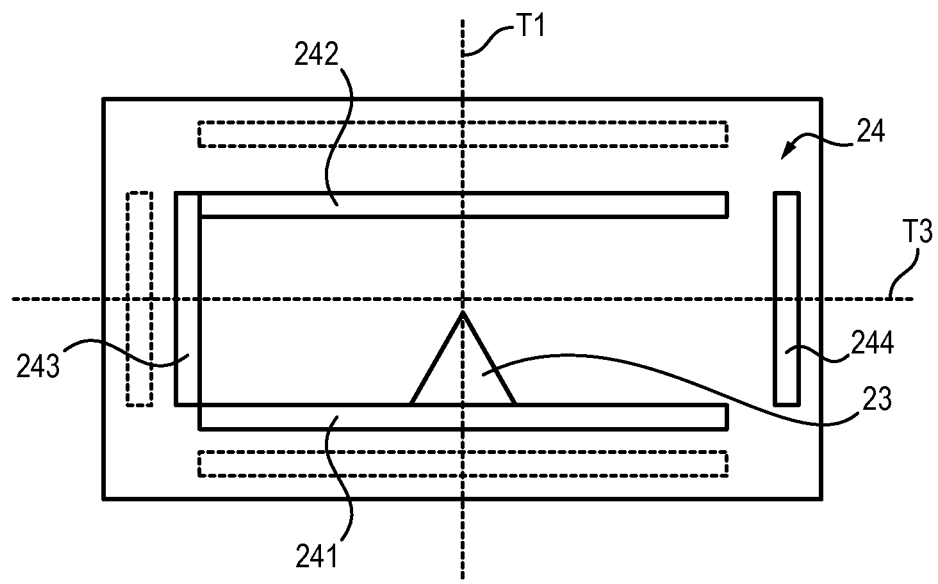
FIG. 5 is an underside view of a collimator with mobile plates, the plates of which are mobile in translation along axes perpendicular to their respective faces according to an embodiment of the present invention.

In an embodiment, the collimator 24 comprises mobile plates 241, 242, 243, 244, the position of the mobile plates defines the illumination zone. The mobile plates 241, 242, 243, 244 are arranged so that the mobile plates' shortest edges are substantially parallel to a main direction of radiation of the radiation source 23. The main direction of radiation is an imaginary line passing through the radiation source 23 and the detector orthogonal to the surface of the radiation source. The plates 241, 242, 243, 244 can be mobile in translation along axes T1 or T3 orthogonal to their respective faces (see FIG. 5).

Figure 6:
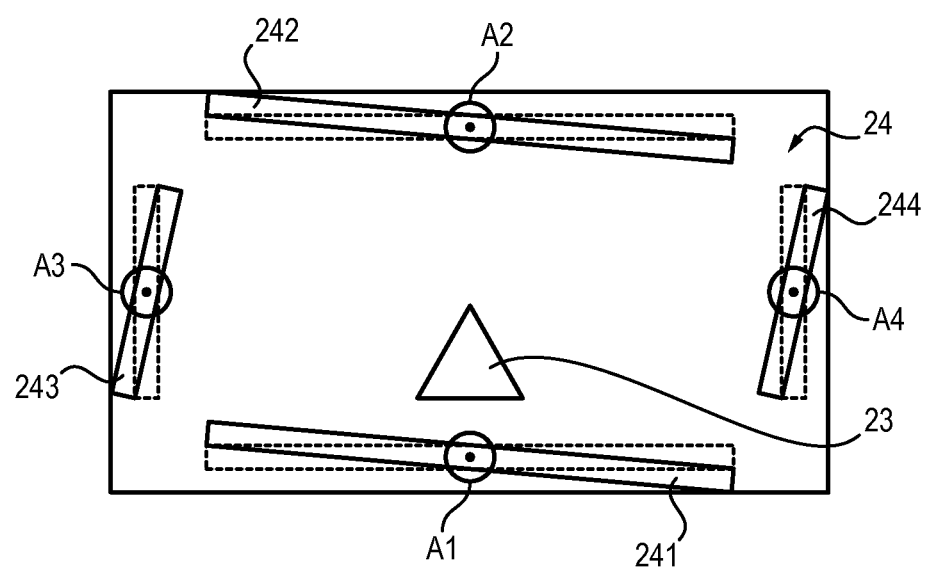
FIG. 6 is an underside view of a collimator with mobile plates, the plates of which are mobile in rotation about axes substantially parallel to the main direction of radiation according to an embodiment of the present invention.

The plates 241, 242, 243, 244 may also be mobile in rotation about axes A1, A2, A3, A4 substantially collinear to the main direction of radiation of the radiation source 23 (see FIG. 6). Such mobility of the plates 241, 242, 243, 244 is advantageous when further reduction of the volume taken up by the region of interest ROI is desired, such as, in an embodiment, if the surgical instrument is elongated along a main axis AIC. This enables the illuminated zone to be defined so that a projection PROI of the reconstructed 3D image of the region of interest ROI has two opposite edges parallel to the image via projection PIC of the main axis AIC of the surgical instrument IC (see FIG. 4).

If the plates 241, 242, 243, 244 are mobile in rotation about axes A1, A2, A3, A4 substantially collinear to the main direction of radiation, it is not necessary to provide for a rotating C-arm 2 that is mobile in rotation about the vertical axis AV perpendicular to the rotational spin axis AS and to a craniocaudal ACC axis and vice versa. Providing these two features does however enable further optimization of the 2D images (also called spin 2D images) of the region of interest ROI used for the reconstruction of the 3D image. These two features, alone or in combination, can improve the acquired 2D medical image by reducing scattering artefacts.

The control 3 drives the radiation source 23 (emission time and radiation energy) and the C-arm 2 (positioning). The control 3 also drives the collimator 24, in an embodiment, the positioning of its plates 241-4. The detector 25 is connected to the control 3 for data transfer. The control 3 also enables the different steps of the method described below to be driven.

The medical imaging system 1 further comprises a memory 4 that is integrated in or connected to the control 3 for recording parameters and medical images. If the memory 4 is located outside the control 3, the memory 4 and the control 3 can be connected via a wire connection, a network or a port (e.g. a USB port). The memory 4 may be a hard disk or SSD, or any other removable, re-write storage means (USB keys, memory cards etc.). The memory 4 may be a ROM/RAM memory of the control, a USB key, a memory card, a memory of a central server.

The medical imaging system 1 further comprises a display 6 connected to the control 3 to display the acquired images and/or acquisition data.

In an embodiment, the display 6 may be separated from the medical imaging system. In an embodiment, the display may be located in a viewing station used by the practitioner to determine a diagnosis from digital medical images.

The display 6 enables a practitioner to visualize the reconstruction and/or the display of the acquired images.

The display 6 is, in an embodiment, a computer display, a monitor, flat screen, plasma screen or any type of commercially known display device.

In an embodiment, there is provided a method for processing images for a 3D display of an organ of a patient in which a surgical instrument is positioned. At least one embodiment of the method is described below with reference to FIG. 7, said at least one embodiment comprising one or more of the following steps. It should be noted that the order of the steps is not absolute and should not be construed in a limiting sense.

In step (a), a region of interest surrounding the surgical instrument inside the organ is determined. The region of interest is a reconstructed volume or a manually determined volume and located immediately around the surgical instrument. In an embodiment, the limits of the region of interest are distant from the surgical instrument by less than about 2 cm, by less than about 1.5 cm, or by less than about 1 cm.

Step (a) is used to reduce the region of the patient's body that would be illuminated by the radiation from the radiation source during the acquisition of the spin 2D images. The patient therefore receives a reduced radiation dose. With conventional tomography imaging, a large region of interest ROI is reconstructed (see FIG. 2) which necessitates a higher radiation dose. On the contrary, with the method according to embodiments of the present invention, the region of interest ROI is reduced according to the required thickness for inclusion of the surgical instrument (see FIGS. 3 and 4). In an embodiment, the region of interest ROI is reduced to the least required thickness for inclusion of the surgical instrument.

In addition, the size reduction of the region of interest to reconstruct in 3D also enables a reduction in the time needed for 3D reconstruction of the image.

The region of interest can be determined using a first series of full field images (e.g. two images taken for two different orientations). In an embodiment, the first series of full field images are taken with the C-arm positioned at a sharp angle (i.e. approximately between ±) 90-90°, the angle 0° corresponding to the front-facing position of the C-arm relative to the patient (antero-posterior position). The full field image means that the collimator is adjusted to obtain the widest illumination possible. In this first series of full field images, the position of the surgical instrument is detected either automatically using an appropriate tool (Gorges, S. et al., "3D Needle Track—a new imaging technique to localize in real time 3D needle position in an interventional room" Geneva, CARS 2010) or manually by the practitioner. Once the position of the needle is detected, a slice (i.e. a volume virtually cut along two parallel planar surfaces in the imaged region) containing the surgical instrument is calculated by back-projection. The slice then forms the region of interest. The median plane of the slice may lie parallel to the ground or obliquely as respectively illustrated in FIGS. 3 and 4.

The region of interest may be determined manually by an operator or the practitioner. Then, the selection is made on the medical imaging system using the control means. The region of interest is a slice parallel to the ground or oblique as respectively illustrated in FIGS. 3 and 4.

If the slice forming the region of interest is parallel to the ground, there is no need for a C-arm rotating about the vertical axis or for a collimator mobile in rotation.

If the slice is oblique, then it is necessary for the C-arm to be able to rotate about the vertical axis and/or for the collimator to have plates mobile in rotation.

If the surgical instrument is thin and elongated, one image is sufficient to calculate the region of interest. This image can be the first of the series of 2D spin images (images obtained by rotating the C-arm about the rotational spin axis).

The C-arm is positioned in an angular position in step (b). The angular position is defined in relation to the rotational spin axis and corresponds to the head-feet axis of the patient. Two different angular positions are obtained by rotating the C-arm about the rotational spin axis. If the C-arm is also mobile along the vertical axis, the angular position of the C-arm is corrected to optimize the image in relation to the orientation of the surgical instrument.

In step (c), the collimator is adjusted to define the illumination zone. The illumination zone is defined by adjusting the collimator. The collimator being adjusted according to the angular position of the C-arm and the region of interest to delimit the illumination zone. Thus, the radiation only passes through the region of the patient's body which needs to be illuminated for 3D image reconstruction of the region of interest.

In step (d), the illumination zone is illuminated by radiation from the radiation source passing through the patient's organ. In step (e), the radiation which has passed through the patient's organ is captured by the detector and recorded thereby enabling the acquisition of a spin 2D image.

For other 2D spin images needed for reconstruction of the 3D image of the region of interest, steps (b) to (e) are repeated for each of the corresponding angular positions. In an embodiment, approximately between 150 and 600 2D spin images are acquired (i.e. the same number of angle positions used).

Once the necessary 2D spin images are acquired, the control generates a 3D image of the region of interest in step (f) and displays the 3D image on the display in step (g). The practitioner does not need to search for the surgical instrument since only the region of interest surrounding the surgical instrument is displayed.

According to an embodiment, the dose received by the patient is reduced through the delimiting of the illumination zone which enables the illumination of only that region of the patient's body which is of interest to the practitioner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for processing images for a 3D display of an organ of a patient in which a surgical instrument is positioned, the method comprising:

(a) using a medical imaging system comprising a rotating C-arm which can be positioned in at least two angular positions, the C-arm comprising a radiation source at one end, a detector at another end, and a collimator between the radiation source and the detector, the collimator comprising a housing and plates, wherein the plates are rotatable relative to the housing;

(b) positioning the C-arm at an angular position;

(c) adjusting the collimator for defining an illumination zone;

(d) illuminating the illumination zone by radiation from the radiation source passing through the organ; and (e) capturing the radiation which has passed through the organ by the detector to acquire a 2D image;

repeating steps (b) to (e) for each angular position of the rotating C-arm, (f) reconstructing a 3D image of a region of interest from the acquired 2D images; and (g) displaying the 3D image, wherein the collimator is adjusted according to the angular position of the C-arm in order to delimit the illumination zone so that the radiation passes only through a zone surrounding the surgical instrument.

2. The method according to claim 1, further comprising:
determining the region of interest corresponding to the position of the surgical instrument inside the organ prior to steps (b) to (e), wherein the collimator is adjusted according to the region of interest.

3. The method according to claim 2, wherein the method further comprises:
determining the region of interest from a first series of full field 2D images of the organ obtained with the C-arm positioned in a first series of angular positions; and
adjusting the collimator for another angular position of the C-arm by theoretically projecting the region of interest onto a full field 2D image corresponding to the other angular position, wherein the position of the plates is calculated from the projection of the region of interest.

4. The method according to claim 3, wherein the plates are mobile in translation along axes orthogonal to respective faces of the plates.

5. The method according to claim 3, wherein:
the C-arm is mobile in rotation about a rotational spin axis corresponding to a head-feet axis of the patient, and about a vertical axis perpendicular to the rotational spin axis and to a craniocaudal axis, wherein the craniocaudal axis passes through the patient's ears; and wherein
the angular position corresponds to positions about the rotational spin axis, and each angular position of the C-arm is corrected by rotation about the vertical axis so that the radiation is substantially perpendicular to a larger surface area of the surgical instrument.

6. The method according to claim 2, wherein the boundaries of the region of interest lie distant from the surgical instrument by less than 2 cm.

7. The method according to claim 6, wherein the boundaries of the region of interest lie distant from the surgical instrument by less than 1.5 cm.

8. The method according to claim 6, wherein the boundaries of the region of interest lie distant from the surgical instrument by less than 1 cm.

9. The method of claim 1, wherein the plates define the illumination zone.

10. A medical imaging system for processing images of an organ of an patient in which a surgical instrument is positioned, the medical imaging system comprising:
a rotating C-arm which can be positioned in at least two angular positions, the C-arm comprising:
a radiation source at one end and configured to emit radiation to illuminate an illumination zone; and
a detector at another end configured to capture the radiation;
a control for positioning the C-arm in an angular position; and
a collimator between the radiation source and the detector comprising a housing and plates;
wherein the collimator is adjustable to define an illumination zone according to the angular position of the C-arm to delimit the illumination zone so that the radiation only passes through a region of interest surrounding the surgical instrument;
wherein the position of the mobile plates defines the illumination zone; and
wherein the plates are rotatable relative to the housing.

11. The system according to claim 10, wherein the plates are mobile in translation along axes substantially orthogonal to respective faces of the plates.

12. The system according to claim 10, wherein the C-arm is mobile in rotation about a rotational spin axis corresponding to a head-feet axis of the patient, and about a vertical axis perpendicular to the rotational spin axis and to a craniocaudal axis, wherein the craniocaudal axis passes through the patient's ears.

13. The system of claim 10, wherein the plates define the illumination zone.

* * * * *